(12) United States Patent
Lenker et al.

(10) Patent No.: US 11,871,960 B2
(45) Date of Patent: Jan. 16, 2024

(54) STEERABLE ENDOLUMINAL PUNCH

(71) Applicant: Indian Wells Medical, Inc., Lake Forest, CA (US)

(72) Inventors: Jay A Lenker, Lake Forest, CA (US); Peter van der Sluis, Palm Springs, CA (US)

(73) Assignee: Indian Wells Medical, Inc., Lake Forest, CA (US)

(*) Notice: Subject to any disclaimer, the term of this patent is extended or adjusted under 35 U.S.C. 154(b) by 401 days.

(21) Appl. No.: 17/189,155

(22) Filed: Mar. 1, 2021

(65) Prior Publication Data
US 2021/0275211 A1    Sep. 9, 2021

Related U.S. Application Data

(63) Continuation of application No. 16/732,717, filed on Jan. 2, 2020, now Pat. No. 10,932,815.

(60) Provisional application No. 62/787,697, filed on Jan. 2, 2019.

(51) Int. Cl.
*A61B 17/34* (2006.01)
*A61B 17/00* (2006.01)
*A61B 90/00* (2016.01)

(52) U.S. Cl.
CPC .... *A61B 17/3403* (2013.01); *A61B 17/00234* (2013.01); *A61B 17/3415* (2013.01); *A61B 90/36* (2016.02); *A61B 90/39* (2016.02); *A61B 2017/00243* (2013.01); *A61B 2017/00305* (2013.01); *A61B 2017/00318* (2013.01); *A61B 2017/3413* (2013.01); *A61B 2017/3425* (2013.01); *A61B 2090/374* (2016.02); *A61B 2090/376* (2016.02); *A61B 2090/378* (2016.02); *A61B 2090/3966* (2016.02)

(58) Field of Classification Search
CPC ............ A61B 90/39; A61B 2090/3904; A61B 2090/392; A61B 2090/3937; A61B 2090/3954; A61B 2090/3966
See application file for complete search history.

(56) References Cited

U.S. PATENT DOCUMENTS

| | | | |
|---|---|---|---|
| 2006/0116573 A1* | 6/2006 | Field | A61B 90/39 600/431 |
| 2011/0295206 A1* | 12/2011 | Gurley | A61B 6/12 604/164.1 |
| 2014/0142418 A1* | 5/2014 | Gurley | A61M 25/09 600/424 |

* cited by examiner

*Primary Examiner* — Mohamed G Gabr
(74) *Attorney, Agent, or Firm* — Crockett & Crockett, PC; K. David Crockett, Esq.

(57) ABSTRACT

Methods for performing certain medical procedures wherein a steerable endoluminal punch is used to not only gain access but to create a channel or punch through tissue, thus facilitating follow-up therapeutic procedures. The distal end of the steerable endoluminal punch is controllably articulated by the operator using a control device at the proximal end.

2 Claims, 3 Drawing Sheets

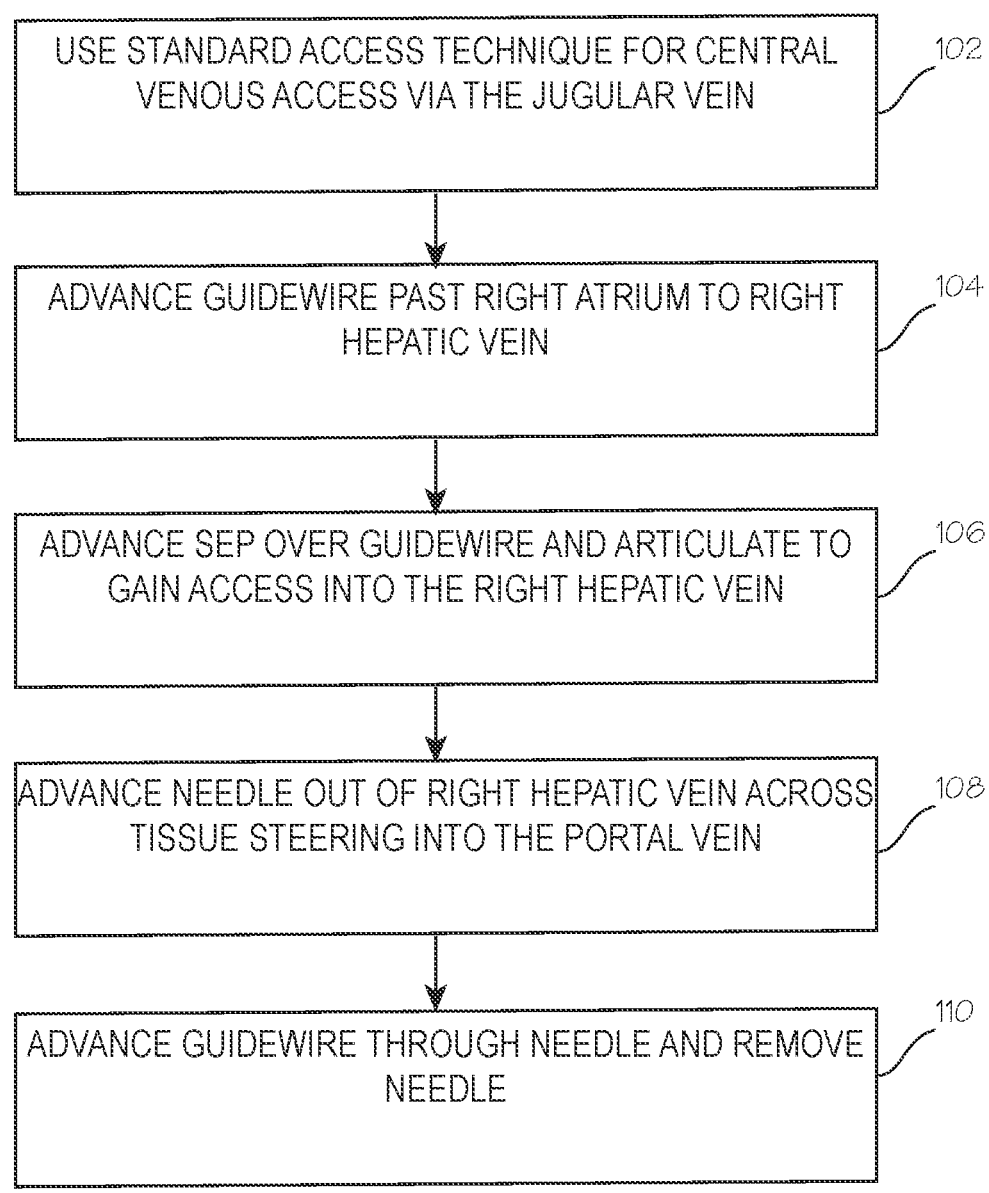

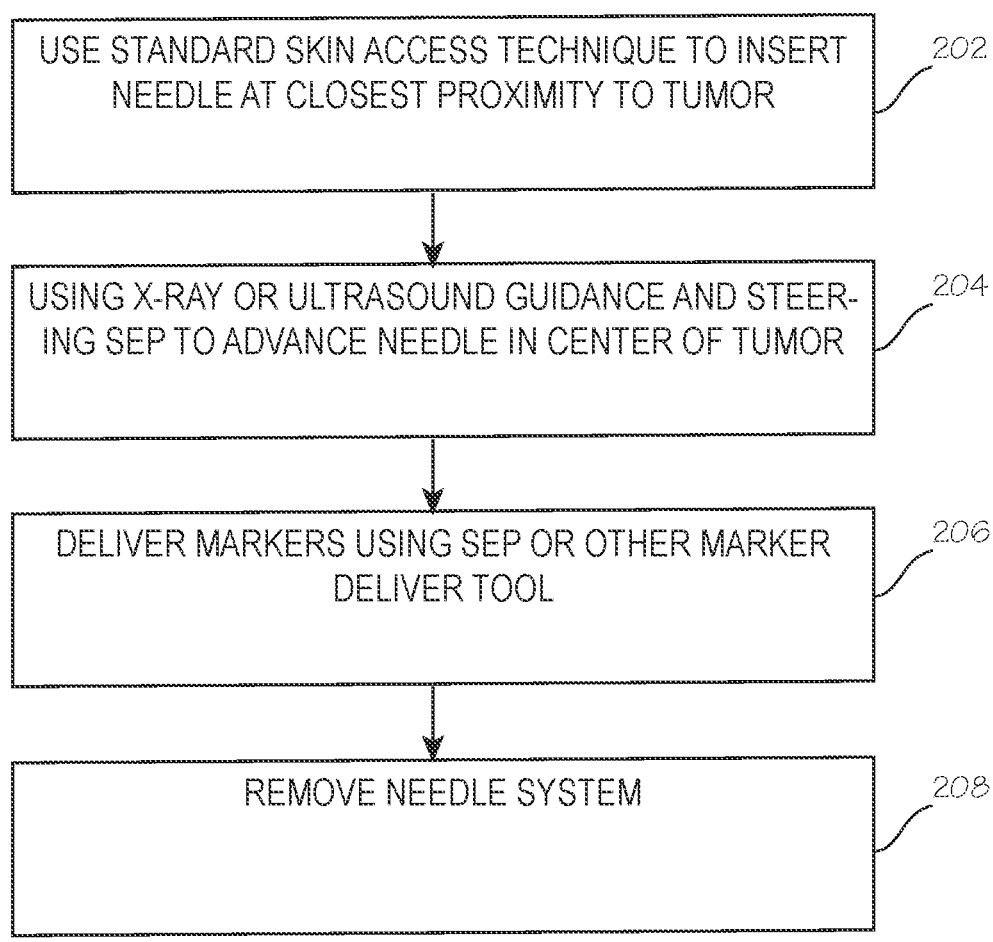

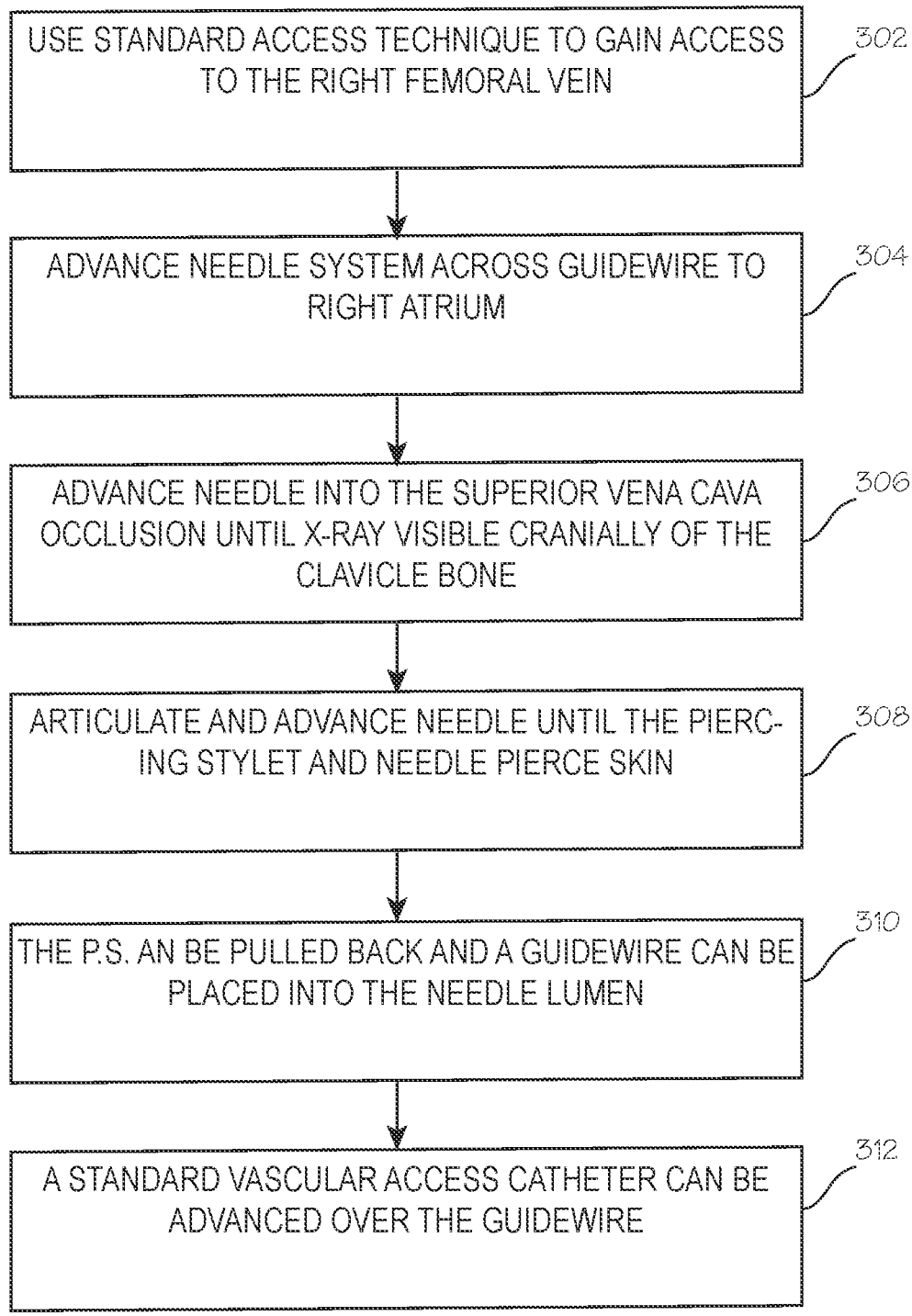

STEERABLE ENDOLUMINAL PUNCH

This application is a continuation of U.S. application Ser. No. 16/732,717, filed Jan. 2, 2020, now U.S. Pat. No. 10,932,815, which claims priority to U.S. Provisional Application 62/787,697, filed Jan. 2, 2019.

FIELD OF THE INVENTION

The inventions described below relate to devices and methods for performing endoluminal access to the cardiovascular system or other body vessels or body lumens, especially procedures performed in the fields of cardiology, radiology, electrophysiology, urology, and surgery.

BACKGROUND

Procedures are currently performed to perform tissue biopsy, place shunts in the liver as well as to place radiopaque markers in body tissue for identification, mapping, or treatment of tumors. Furthermore, procedures are performed to gain percutaneous access to the vasculature but access is sometimes restricted by the presence of anatomic or pathological anomalies.

SUMMARY OF THE INVENTIONS

A steerable endoluminal punch (SEP) has been described by the inventors in various patent applications. This specification applies that steerable endoluminal punch to certain other medical procedures. The steering aspect of this stiff, sharp-tipped needle, allows for precise placement, high bending force generation, and confident guidance to the target location. These other medical procedures represent actual uses but the steerable endoluminal punch is also useful for many other procedures within the human body.

BRIEF DESCRIPTION OF THE DRAWINGS

FIG. 1 illustrates a flow chart describing the steps involved in placing a shunt in the vasculature of the liver using a steerable endoluminal punch, according to an embodiment of the invention;

FIG. 2 illustrates a flow chart describing the steps involved in placing radiopaque markers within or proximate tumors using a steerable articulating needle, according to an embodiment of the invention; and FIG. 3 illustrates a flow chart describing the steps involved in performing an inside-out vascular access procedure using an articulating needle, according to an embodiment of the invention.

DETAILED DESCRIPTION

In accordance with current terminology pertaining to medical devices, the proximal direction will be that direction on the device that is furthest from the patient and closest to the user. The distal direction is that direction closest to the patient and furthest from the user. These directions are applied along the longitudinal axis of the device, which is generally an axially elongate structure having one or more lumens or channels extending through the proximal end to the distal end and running substantially the entire length of the device.

In an embodiment, the device described herein is an endoluminally, transvascularly, or endovascularly placed tissue punch, with internal deflectability or the ability to articulate, at its distal end, in a direction away from its longitudinal axis. The punch can also be termed a catheter, needle, tissue incision apparatus, or cannula. The punch is generally fabricated from stainless steel and comprises an outer tube, an intermediate tube, a central stylet wire, and a distal articulating region. The deflecting or articulating mechanism is integral to the punch. Certain punch designs can comprise a single tube or, in other embodiments, a wire or rod with no lumen. The punch, needle, or catheter is sufficiently rigid so as to be able to exert clinically significant on-axis force on the distal end by action at the proximal end, even when the punch is articulated or bent off-axis. In other embodiments it can be used as an internal guidewire or internal guide catheter. The punch is useful for animals, including mammals and human patients and is routed through body lumens or other body structures to reach its target destination.

In an embodiment, the punch comprises an inner core wire or stylet, an intermediate tube and an outer tube. In an embodiment, the stylet can be removable or non-removable. The punch further comprises a hub at its proximal end which permits grasping of the punch and also includes a stopcock or valve to serve as a lock for the stylet, or inner core wire, as well as a valve for control of fluid passage into and out from the innermost lumen within which the stylet or inner core wire resides. The proximal end further comprises one or more control handles or knobs to manipulate the amount of articulation at the distal end of the catheter. The proximal end can comprise deflection measuring displays, gauges, or the like. The proximal end further can be terminated with one or more female Luer or Luer lock ports, which are suitable for attachment of pressure monitoring lines, dye injection lines, vacuum lines, a combination thereof, or the like.

In another embodiment, steerability can be obtained using actuators on the surface or within the interior of the cannula to force bending of the cannula. These actuators can be typically electrically powered. In an embodiment, an actuator can comprise electrical leads, a power source, a compressible substrate, and shape memory materials such as nitinol. Such actuators may be distributed along the length of the cannula. The actuators may be placed so as to oppose each other. Opposing actuators are activated one at a time and not simultaneously and can generate a steering effect or back and forth motion.

Other embodiments of the inventions comprise methods of use. In one embodiment, access to liver tissue and vasculature can be obtained to permit, for example, delivery of a shunt. The procedure, summarized in FIG. 1, can comprise the following steps:

Gain access to the jugular vein by way of a percutaneous stick (like a Seldinger technique) or a cutdown, step 102.

Route a guidewire (about 0.018 to 0.021, or preferably 0.035 to 0.040, inches in diameter for example) through a percutaneous access device retrograde down through the inferior vena cava.

Route the guidewire into the hepatic vein, step 104.

Optionally, remove the percutaneous access device.

Leave the guidewire in place.

Prepare the SEP by inserting it through the central lumen of a dilator positioned within the central lumen of a delivery catheter.

Alternatively, advance the dilator and catheter over the guidewire first and then insert the SEP therethrough.

Advance the SEP, dilator and catheter over the guidewire using the internal lumen of the SEP to engage the guidewire.

Using controls at the proximal end of the SEP, articulate the distal end of the SEP to provide curvature as required for ease of access, step 106.

Orient the SEP using orientation markers on the hub of the SEP to indicate the direction of tip curvature.

Monitor the tip curvature of the SEP using fluoroscopic imaging, ultrasound imaging, MRI, a combination thereof, or the like.

Position the tip of the SEP just inside the distal end of the dilator.

Position the distal end of the dilator in the distal hepatic vein with the tip against the wall of the vein.

Expose the sharp distal tip of the SEP beyond the tip of the dilator and puncture through the wall of the distal hepatic vein.

Further adjust the curvature of the SEP and catheter using the control mechanisms on the SEP to provide steering as necessary.

(If penetration of tissue is difficult, the use of a sharp, central stylet or energized piercing stylet may be brought to bear to increase the tissue penetration capabilities of the SEP.)

Advance the SEP through the parenchymal tissue until it is positioned across the hepatic parenchyma and toward a target portal vein, step 108.

Penetrate the wall of the portal vein and drive the SEP into the lumen of the portal vein.

Application of suction at the proximal end of the SEP or catheter can be used to verify placement by visualization of blood. Also, injection of contrast media can be used to verify positioning.

Insert or maintain the position of a guidewire bridging the hepatic vein and the portal vein, step 110.

Maintain the catheter and dilator within the target portal vein, as required, for further diagnostic or interventional procedures.

Such interventional procedures can include, but not be limited to, placement of a shunt.

The system has the advantage of using fewer devices than may be required currently. The SEP provides stiffness, column strength, and steerability to facilitate the procedure and increase the accuracy of targeting.

In other embodiments, the SEP can comprise an angioplasty-type balloon, affixed thereto, for use in enlarging the tissue track.

In other embodiments, the SEP can comprise radiopaque markers such as those made from gold, platinum, iridium, tantalum, or the like to facilitate visualization, steering, targeting, and the like.

In other embodiments, the SEP can comprise a blunt central stylet and be placed through the lumen of a catheter and dilator that have had the guidewire removed. The blunt central stylet is protective and may be removed after full advancement of the SEP to the target location is achieved.

In yet other embodiments, the SEP can be operably connected to a radiofrequency (RF) generator, high intensity focused ultrasound (HIFU) microwave generator, DC power source for Ohmic heating, cryoablation capability, or the like, to facilitate tissue penetration.

In other embodiments, a shunt, comprising a stiff wall and resistant to leakage, such as, but not limited to, a covered stent, a stent-graft, a semi-rigid PTFE tube, or the like, can be disposed over the SEP or its delivery catheter such that the stent-graft can be deployed within the parenchyma without having to remove the SEP and catheter and replace it with a specialized delivery system for the shunt. The shunt can be full size, balloon expandable, self-expanding, or the like.

In similar fashion, the SEP can be used to penetrate tissue from a simple percutaneous stick, step 202, directly into target tissue of some importance, such as carcinogenic tissue, tumor, or the like. The SEP advancement and targeting are guided by fluoroscopy, MRI, ultrasound, or the like, step 204. The SEP can comprise ring shaped radiopaque markers disposed over its exterior. These radiopaque markers can be deployed from the SEP by use of an internal actuator which is controlled by a feature on the proximal hub of the SEP, step 206. The radiopaque markers can be used for targeting therapies at the tumor or for serving as antenna for energy to generate heat within the tumor. In this embodiment, the SEP is generally routed through tissue but not necessarily through vasculature. The SEP can be articulated throughout the procedure to optimize targeting and marker placement. The SEP is removed from the patient after placement of the markers, step 208. FIG. 2 summarizes the biopsy marker placement procedure using the SEP.

The SEP can be further configured with a side window to permit acquisition of tissue biopsies. Tissue, drooping into the window can be severed by a trefine-like structure within the SEP and retained within the window for analysis. One particular use of a SEP biopsy device is for acquisition of bone marrow biopsies, for example in the pelvis. A rigid trocar can be used to penetrate the bone, after which the trocar is removed allowing for SEP articulation and the ability to reach tissue that cannot be accessed with a straight biopsy device.

In yet another embodiment, the SEP can be routed through the right femoral vein, for example, in patients with venous blockage and general lack of proper access to the vasculature. The SEP is inserted through an access point in the right femoral vein created by percutaneous access or a cutdown, step 302. The SEP is designed and configured in a flexible manner to easily navigate tortuous vasculature. The SEP possesses column strength even when exhibiting flexibility. FIG. 3 summarizes the inside out access procedure using the SEP.

The SEP can be routed through the right atrium of the heart into the SVC and any blockage therein, step 304. A piercing stylet, either static or energized, can be used to penetrate any blockage. The tip of the SEP can be disposed cranially of the clavicle bone step, 306. It can next be articulated such that it points laterally to some degree, step 308. The piercing stylet can be used to drive a channel through tissue with that channel emerging from the patient such that reverse access to the central venous system, may be achieved through the channel. The SEP is driven out through the skin such that the lumen is available for access with a guidewire, step 310. The piercing stylet can be removed and replaced with a guidewire to establish the channel for retrograde access with standard vascular access catheters, step 312.

In some embodiments, the SEP can have an external diameter of about 0.050 inches, with a central guidewire diameter capacity of about 0.021 inches. In other embodiments, the SEP can comprise an external diameter of about 0.060 to 0.075 inches in diameter, and preferably about 0.063 to 0.073, thus allowing for a central guidewire diameter of 0.035 inches or larger.

In some embodiments, the SEP can comprise measuring capability to provide feedback to the user or a computer regarding parameters such as, but not limited to, tip deflection angle, tip deflection percentage, axial location, ultrasound imaging (both 2-D and 3-D static as well as real-time 3-D), and the like. The SEP can comprise a gauge or readout for the deflection data or it can be operationally coupled to a computer which can analyze deflection, position, and the like. A gauge system can comprise a linkage from a moving part of the hub, including but not limited to, a jackscrew component which moves linearly and axially, a rotation counter on a control knob, a force measuring component, and the like.

For example, the SEP can be used to deliver access devices and implants for the purpose of creating a shunt between two or more blood vessels. In some embodiments, the two or more blood vessels comprise a vein and an artery. In other embodiments, the two or more blood vessels are located in the leg. In some embodiments, the blood vessels are being shunted to permit greater blood pressure to be applied to the cerebro-vasculature or to improve oxygenation of various body tissues. The SEP permits high precision access to tissue and vasculature separated from the vessel in which the SEP originally resides, following crossing of tissue separating the two or more blood vessels.

In some embodiments, the SEP can be steered by manual action on the part of a user such as an interventional cardiologist, radiologist, or the like. In other embodiments, the SEP can comprise a mechanism to permit articulation due to action and forces applied to the distal tip by way of electric, hydraulic, or pneumatic motors. The motors can be controlled by a manual switch for the purpose of ease of bending. In these cases, the manual switch can control the SEP to increase or decrease the bend, to advanced or retracted relative to a sheath or landmark, etc., or a combination thereof. The motors can be controlled by wired bus or by wireless means such as radio, Bluetooth, WiFi, ultrasound, or the like. The motors can be controlled by way of a computer which can guide articulation in response to anatomical landmark sensing, fluoroscopy, echocardiography, or the like. The computer can include, but is not limited to, standard personal computer, laptop computer, cell smartphone, tablet computer, dedicated controller, or the like. Input to the computer can be manual or could include voice control, such as "bend the tip to 80 degrees", etc. The system can provide feedback to the user either by audio means, visual means, hepatic means, or the like.

The SEP is configured to provide selective user control over tip bending, in combination with pre-set capabilities, figured into the design of the distal tip. The SEP is capable of being articulated by itself, without the need for any external guiding or steering sheaths or introducers. The SEP can be used with "dumb" introducers to perform its function at a fraction of the cost associated with a steerable introducer or sheath. Once bent, or articulated, the SEP can be advanced distally, causing the curved distal end to puncture tissue to which it is exposed. If a stable curve is required, a piercing stylet can be utilized within the lumen of the SEP to puncture tissue using the SEP and introducer as stability generators. Given the possibility of providing complex curves, the SEP can be made to curve along several axes or in different ways along its distal length. The SEP can also be used with introducers whose tip can comprise additional cutting mechanisms which can then be actuated to increase the size of the tip incision and facilitate passage through tough, fibrous tissue.

In yet other embodiments, the SEP can be used to steer a biopsy punch system into a specific location, which cannot be generally reached with a non-steerable biopsy punch. The SEP can be advanced using a rigid trocar, through tissue, etc. The rigid trocar can be removed to allow the SEP to be bent or articulated laterally so that biopsy tissue samples can be aspirated, through, for example, one or more side windows near the tip of the device. One example of use for this type of device is to take bone marrow biopsies in the hip or pelvic region of a patient. The device can be pounded through the bone into the marrow using a rigid, strong central trocar. The trocar can be removed from the central lumen leaving the SEP in the patient. The SEP can then be articulated laterally to target hard-to-reach areas that might provide biopsy specimens.

The present invention may be embodied in other specific forms without departing from its spirit or essential characteristics. The described embodiments are to be considered in all respects only as illustrative and not restrictive.

What is claimed is:

1. A method of achieving vascular access through an inside out procedure comprising:
   creating a percutaneous access point to a femoral vein;
   inserting a steerable endoluminal punch into the percutaneous access point;
   advancing the steerable endoluminal punch through a blockage in the vasculature and to a position cranial to the clavicle;
   articulating the steerable endoluminal punch such that its distal tip is curved and directed toward the surface of the skin;
   advancing a sharp central stylet through the steerable endoluminal punch and out through the skin of the patient;
   advancing the steerable endoluminal punch such that its distal end is exposed outside the patient's skin;
   removing the sharp central stylet;
   inserting a guidewire through the steerable endoluminal punch; and
   removing the steerable endoluminal punch leaving the guidewire in place to facilitate reverse access to the patient's vasculature.

2. A method of achieving vascular access through an inside out procedure comprising:
   creating a percutaneous access point to a femoral vein;
   inserting a steerable endoluminal punch into the percutaneous access point;
   advancing the steerable endoluminal punch through a blockage in the vasculature and to a position cranial to the clavicle;
   articulating the steerable endoluminal punch such that its distal tip is curved and directed toward the surface of the skin;
   advancing a blunt central stylet through the steerable endoluminal punch and out through the skin of the patient;
   advancing the steerable endoluminal punch such that its distal end is exposed outside the patient's skin;
   removing the blunt central stylet;
   inserting a guidewire through the steerable endoluminal punch; and
   removing the steerable endoluminal punch leaving the guidewire in place to facilitate reverse access to the patient's vasculature.

* * * * *